US00PP23012P2

(12) United States Plant Patent
Smith

(10) Patent No.: US PP23,012 P2
(45) Date of Patent: Sep. 4, 2012

(54) ***CHRYSANTHEMUM* PLANT NAMED 'CIFZ0028'**

(50) Latin Name: *Chrysanthemum×morifolium*
Varietal Denomination: CIFZ0028

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/385,455

(22) Filed: Feb. 21, 2012

(51) Int. Cl.
*A01H 5/00* (2006.01)

(52) U.S. Cl. ..... Plt./294

(58) Field of Classification Search ..... Plt./294
See application file for complete search history.

*Primary Examiner* — June Hwu
*Assistant Examiner* — Louanne Krawczewicz Myers
(74) *Attorney, Agent, or Firm* — Joshua L. Price

(57) ABSTRACT

A new *Chrysanthemum* plant named 'CIFZ0028' particularly distinguished by the medium to large sized white anemone-type inflorescences with yellow and white discs, medium green foliage, round and mounded plant habit, with a natural flowering season response of early September.

1 Drawing Sheet

Latin name of the genus and species of the plant claimed: *Chrysanthemum×morifolium.*

Varietal denomination: 'CIFZ0028'.

BACKGROUND OF THE NEW PLANT

The present invention comprises a new *Chrysanthemum*, botanically known as *Chrysanthemum×morifolium*, and hereinafter referred to by the variety name 'CIFZ0028'.

'CIFZ0028' is a product of a planned breeding program. The new cultivar has medium to large sized white anemone-type inflorescences with yellow and white discs, medium green foliage, round and mounded plant habit, with a natural flowering season response of early September.

'CIFZ0028' originated from a hybridization made in September 2007 in a greenhouse in Amanecer, Columbia. The female parent was the unpatented, proprietary plant designated '03-M220', with light yellow inflorescences, a larger diameter disk, larger plant habit, and a black cloth flowering response that is about 3 weeks slower than that of 'CIFZ0028'.

The male parent of 'CIFZ0028' was the unpatented, proprietary plant designated as '04-M222', with similar white inflorescences, smaller disc diameter, and a blackcloth flowering response that is about 1 week faster than that of 'CIFZ0028'. The resultant seed was sown and grown outdoors in October 2008 in Alva, Fla. USA.

'CIFZ0028' was selected as one flowering plant within the progeny of the stated cross in March 2009 in Alva, Fla.

The first act of asexual reproduction of 'CIFZ0028' was accomplished when vegetative cuttings were propagated from the initial selection in May 2009 in Alva, Fla.

BRIEF SUMMARY OF INVENTION

Horticultural examination of plants grown from cuttings of the plant initiated in May 2009, and continuing thereafter, has demonstrated that the combination of characteristics as herein disclosed for 'CIFZ0028' are firmly fixed and are retained through successive generations of asexual reproduction.

'CIFZ0028' has not been observed under all possible environmental conditions. The phenotype may vary significantly with variations in environment such as temperature, light intensity, and day length.

A Plant Breeder's Right for this cultivar was applied for in Canada on Feb. 24, 2011, No. 11-7181. 'CIFZ0028' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0028' with colors being as true as possible with an illustration of this type. The photographic drawing shows a flowering potted plant of the new variety and a close-up of the inflorescences.

DETAILED BOTANICAL DESCRIPTION

The plant descriptions, measurements, and aforementioned photographs were taken outdoors in Gilroy, Calif. in early August 2011. The plants were growing in an outdoor potted plant trial, in one gallon pots, in full sun. These plants were approximately 9-10 weeks of age.

Color references are made to The Royal Horticultural Society Colour Chart (R.H.S.) 2001.

TABLE 1

DIFFERENCES BETWEEN THE NEW VARIETY 'CIFZ0028' AND A MOST SIMILAR VARIETY FOR COLOR

| | 'CIFZ0028' | 'Yovanna' (U.S. Plant Pat. No. 20,231) |
|---|---|---|
| Ray floret color: | White | White |
| Inflorescence type: | Anemone | Daisy |
| Inflorescence size: | Medium/large | Medium |

TABLE 1-continued

DIFFERENCES BETWEEN THE NEW VARIETY 'CIFZ0028' AND A MOST SIMILAR VARIETY FOR COLOR

| | 'CIFZ0028' | 'Yovanna' (U.S. Plant Pat. No. 20,231) |
|---|---|---|
| Plant shape: | Sphere/mounded | Mounded |
| Plant size: | Small | Medium |
| Natural season flowering response: | Early September | Mid September |

TABLE 2

DIFFERENCES BETWEEN THE NEW VARIETY 'CIFZ0028' AND A MOST SIMILAR VARIETY FOR INFLORESCENCE FORM

| | 'CIFZ0028' | 'Yomonica' (U.S. Plant Pat. No. 14,301) |
|---|---|---|
| Inflorescence form: | Anemone | Anemone |
| Ray floret color: | White | Light yellow |
| Plant size: | Small | Medium/large |
| Natural season flowering response: | Early September | Later September |

Plant:

*Form, growth and habit.*—Herbaceous, garden-type, stems upright and outwardly spreading, freely branching, strong and moderately vigorous growth habit.

*Plant height.*—14.0-17.0 cm.

*Plant height* (*inflorescence included*).—17.0-21.0 cm.

*Plant width.*—36.0-38.0 cm.

Roots:

*Number of days to initiate roots.*—About 4 days at about 22 degrees C.

*Number of days to produce a rooted cutting.*—4-6 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Closest to RHS 137B.

*Mature, leaf color, upper surface.*—Closest to RHS 137A.

*Lower surface.*—Closest to RHS 137B.

*Length.*—4.3-4.5 cm.

*Width.*—3.3-3.6 cm.

*Shape.*—Ovate.

*Base shape.*—Attenuate.

*Apex shape.*—Mucronulate.

*Margin.*—Palmately lobed; irregularly incised, and serrate.

*Texture, upper surface.*—Bifid T-shaped hairs.

*Lower surface.*—Bifid T-shaped hairs.

*Color of veins, upper surface.*—RHS 144B basally, becoming indistinct.

*Color of veins, lower surface.*—RHS 144B basally, becoming indistinct.

*Petiole color.*—RHS 144B.

*Length.*—0.5-0.8 cm.

*Diameter.*—0.3 cm.

*Texture.*—Bifid T-shaped hairs.

Stem:

*Quantity of main branches per plant.*—About 10.

*Color of stem.*—RHS 146A but appears lighter due to hairs.

*Length of stem.*—10.0-12.0 cm.

*Diameter.*—0.4 cm.

*Length of internodes.*—0.75-1.5 cm.

*Texture.*—Bifid T-shaped hairs.

*Color of peduncle.*—RHS 146A.

*Length of peduncle.*—6.5-8.0 cm.

*Peduncle diameter.*—0.2 cm.

*Texture.*—Bifid T-shaped hairs.

Inflorescence:

*Type.*—Compositae, solitary anemone-type inflorescences, borne terminally above foliage, ray florets arranged acropetally on a capitulum.

*Quantity of inflorescences per plant.*—80-100 with about 100 buds.

*Lastingness of individual blooms on the plant showing.*—More than 6 weeks from first color.

*Fragrance.*—Slightly spicy.

Bud (just when opening/showing color):

*Color.*—Closest to RHS 155B.

*Length.*—0.7-1.4 cm.

*Width.*—1.1-1.3 cm.

*Shape.*—Oblate.

Immature infloresence:

*Diameter.*—5.4-5.6 cm.

*Color of ray florets, upper surface.*—RHS 155D but whiter.

*Lower surface.*—RHS 155D but whiter.

Mature infloresence:

*Diameter.*—7.0-7.8 cm.

*Depth.*—1.3-1.5 cm.

*Total diameter of disc.*—2.5-3.0 cm.

*Receptacle height.*—0.5 cm.

*Receptacle diameter.*—0.5-0.6 cm.

*Receptacle color.*—RHS 144B.

Ray florets:

*Quantity of florets.*—36-42 in 2 whorls.

*Color of florets, upper surface.*—RHS 155D but whiter.

*Lower surface.*—RHS 155D but whiter.

*Length.*—3.2-3.3 cm.

*Width.*—0.7 cm.

*Shape.*—Elliptical.

*Apex shape.*—Obtuse to irregularly emarginate or praemorse.

*Base.*—About Cuneate or Truncate.

*Margin.*—Entire.

*Texture, upper surface.*—Papillose.

*Lower surface.*—Papillose.

Disc florets:

*Average quantity of florets.*—About 130 mature and 10-15 immature.

*Immature florets.*—Color of florets: RHS 2C with RHS 2B basal spot and RHS 13B at the apex.

*Length.*—0.5-0.6 cm.

*Width.*—0.1 cm.

*Mature florets.*—Color of florets: RHS 155A to RHS 155B with spots of RHS 3B basally and at the apex.

*Length.*—1.1-1.3 cm.

*Width.*—0.2-0.3 cm at the widest point.

*All disc florets.*—Shape: Tubular, elongated.

*Apex shape.*—Acute, 5 pointed.

Phyllaries:

*Quantity.*—20-25.

*Color, upper surface.*—Between RHS 147A and RHS 147B.

*Lower surface.*—RHS 147B.

*Length.*—0.6-0.7 cm.

*Width.*—0.2 cm.

*Shape.*—Lanceolate.

*Apex shape.*—Acute.

*Base.*—Fused.

*Margins.*—Entire; some papery.

*Texture, upper surface.*—Glabrous.

*Lower surface.*—Bifid T-shaped hairs.

Reproductive organs:

*Pistil.*—1, found on both types of florets.

*Length.*—0.6 cm.

*Style color.*—RHS 1C.

*Style length.*—0.5 cm.

*Stigma color.*—RHS 13A.

*Stigma shape.*—Bi-parted.

*Ovary color.*—RHS 157B.

*Ovary length.*—0.05 cm.

*Ovary width.*—0.075 cm.

*Stamens.*—4, found on only on the disc florets.

*Color of filaments.*—RHS 1C.

*Length filaments.*—0.2 cm.

*Anther color.*—RHS 17D but very translucent looking.

*Anther length.*—0.1 cm.

*Anther shape.*—Oblong.

*Pollen amount.*—None found.

Fertility/seed set: Not observed to date.

Disease and pest resistance: Not observed to date.

What is claimed is:

1. A new and distinct variety of *Chrysanthemum* plant named 'CIFZ0028' substantially as illustrated and described herein.

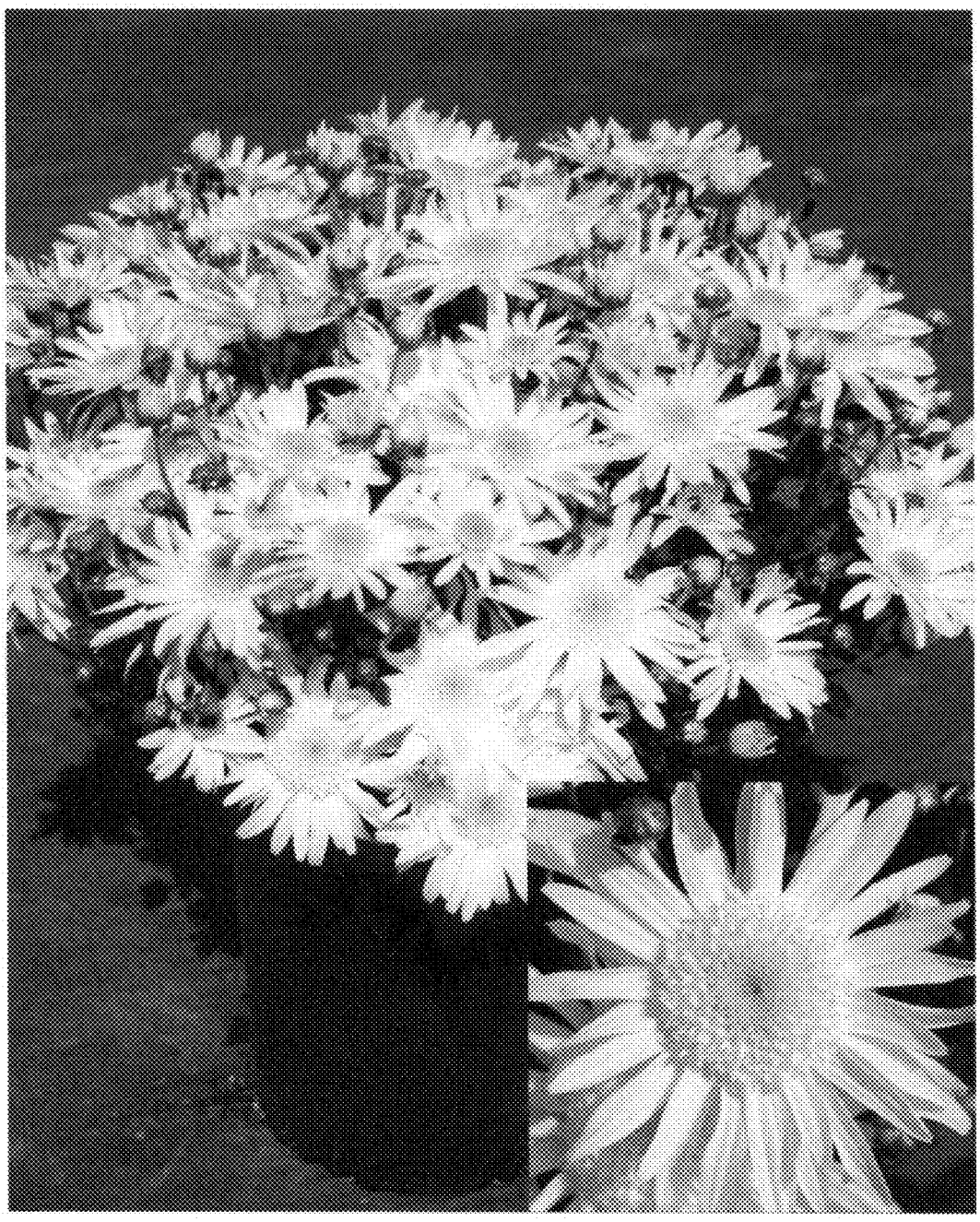

* * * * *